US008662889B2

(12) United States Patent
Baker (10) Patent No.: US 8,662,889 B2
(45) Date of Patent: Mar. 4, 2014

(54) ARCH BARS FOR USE IN MAXILLOFACIAL SURGERY AND ORTHODONTICS

(75) Inventor: Stephen B. Baker, McLean, VA (US)

(73) Assignee: Georgetown University, Washington, DC (US)

( * ) Notice: Subject to any disclaimer, the term of this patent is extended or adjusted under 35 U.S.C. 154(b) by 65 days.

(21) Appl. No.: 13/061,119

(22) PCT Filed: Aug. 27, 2009

(86) PCT No.: PCT/US2009/055212
§ 371 (c)(1),
(2), (4) Date: Feb. 25, 2011

(87) PCT Pub. No.: WO2010/025263
PCT Pub. Date: Mar. 4, 2010

(65) Prior Publication Data
US 2011/0152951 A1    Jun. 23, 2011

Related U.S. Application Data

(60) Provisional application No. 61/092,294, filed on Aug. 27, 2008.

(51) Int. Cl.
*A61C 3/00* (2006.01)

(52) U.S. Cl.
USPC .............................................. 433/18; 433/19

(58) Field of Classification Search
USPC .......... 433/6–7, 18–24, 215; 606/70, 71, 280, 606/283–286, 105, 291
See application file for complete search history.

(56) References Cited

U.S. PATENT DOCUMENTS

| 2,481,177 | A | * | 9/1949 | Tofflemire | 602/5 |
|---|---|---|---|---|---|
| 2,502,902 | A | * | 4/1950 | Tofflemire | 606/54 |
| 3,474,779 | A | | 10/1969 | Wall, Jr. | |
| 4,015,334 | A | * | 4/1977 | Moss | 433/17 |
| 4,202,328 | A | | 5/1980 | Sukkarie | |
| 4,230,104 | A | * | 10/1980 | Richter | 433/18 |
| 4,639,219 | A | * | 1/1987 | Gagin | 433/22 |
| 4,764,112 | A | | 8/1988 | Bergersen | |
| 4,904,188 | A | | 2/1990 | Baurmash | |
| 5,139,497 | A | * | 8/1992 | Tilghman et al. | 606/285 |
| 5,984,925 | A | * | 11/1999 | Apgar | 606/284 |
| 6,086,365 | A | * | 7/2000 | Fields | 433/18 |

(Continued)

OTHER PUBLICATIONS

Bolourian et al., "Transoral 2.0-mm Miniplate Fixation of Mandibular Fractures Plus 2 Weeks' Maxillomandibular Fixation: A Prospective Study," *J Oral Maxillofac Surg* 60:167-170, 2002.

(Continued)

*Primary Examiner* — Yogesh Patel
(74) *Attorney, Agent, or Firm* — Klarquist Sparkman, LLP (57) ABSTRACT

A dental arch bar system includes upper and lower dental arch bars having movable transverse arms and ligature connectors. Fasteners secure the transverse arms to a subject's maxilla and mandible. Ligatures are secured around upper and lower ligature connectors to achieve intermaxillary fixation. A method is also disclosed for using the arch bar system to achieve intermaxillary fixation by securing the arch bars against opposing dental arches with ligature connectors of the upper and lower arch bar generally aligned. In some embodiments, a single dental arch bar is utilized and one or more ligature connectors (such as screws) are fixed directly in the bone of the opposite jaw. Ligatures then are secured to arch bar ligature connectors and the opposing ligature connectors.

14 Claims, 8 Drawing Sheets

(56) References Cited

U.S. PATENT DOCUMENTS

| | | | |
|---|---|---|---|
| 6,256,884 B1 | 7/2001 | Takeuchi et al. | |
| 6,257,884 B1 | 7/2001 | Chang | |
| 6,358,255 B1 | 3/2002 | Testa | |
| 6,382,966 B1* | 5/2002 | Aknin | 433/10 |
| 6,652,530 B2* | 11/2003 | Ip et al. | 606/284 |
| 7,182,785 B2 | 2/2007 | Elsalanty et al. | |
| 7,235,077 B1 | 6/2007 | Wang et al. | |
| 7,351,058 B2 | 4/2008 | Fore et al. | |
| 8,118,850 B2* | 2/2012 | Marcus | 606/328 |
| 2002/0150856 A1 | 10/2002 | Payton | |
| 2004/0199094 A1 | 10/2004 | Greene et al. | |
| 2005/0282115 A1 | 12/2005 | Gedebou | |
| 2007/0156147 A1* | 7/2007 | Wang et al. | 606/69 |
| 2007/0259306 A1 | 11/2007 | Raines, Jr. et al. | |
| 2008/0118885 A1* | 5/2008 | Devincenzo et al. | 433/10 |
| 2009/0148804 A1* | 6/2009 | Marcus | 433/7 |

OTHER PUBLICATIONS

Coletti et al., "Application of Intermaxillary Fixation Screws in Maxillofacial Trauma," *J Oral Maxillofac Surg* 65:1746-1750, 2007.

Dimitroulis, "Management of Fractured Mandibles Without the Use of Intermaxillary Wire Fixation," *J Oral Maxillofac Surg* 60:1435-1438, 2002.

Gawelin & Thor, "Case Report—Conservative treatment of paediatric mandibular fracture by the use of orthodontic appliance and rubber elastics: report of a case," *Dental Traumatology* 21(1):57-59, 2005. (Abstract Only).

Gibbons et al., "Interesting Case: Arch bar support using self-drilling intermaxillary fixation screws," *British Journal of Oral and Maxillofacial Surgery* 43(5):444, 2005.

Karlis & Glickman, "An Alternative to Arch-Bar Maxillomandibular Fixation," *Plastic and Reconstructive Surgery* 99(6):1758-1759, 1997.

Kim, "Facial Trauma, Maxillary and Le Fort Fractures," *WebMD*, available on the web at: http://emedicine.medscape.com/article/1283568-overview, 2006.

Salama, "Application of IMF Screws in Maxillofacial Trauma: A Pilot Study to Examine Efficacy and Safety," *AAOMS* 60-61, 2005.

Tellioğlu et al., "Maxillomandibular fixation with a combination of arch bars and screws," *Eur J Plast Surg* 21:215-216, 1998.

Terai & Shimahara, "Intermaxillary Fixation Using Thermoforming Plate," *J Oral Maxillofac Surg* 60:1092-1094, 2002.

"Perioperative stabilisation of the occlusion in adults," Synthes GmbH, available on the web at: http://www.synthes.com/oldsite/html/IMF_Screw_Set.4600.0.html.

International Search Report from corresponding International PCT Application No. PCT/US2009/055212 dated Oct. 15, 2009.

Written Opinion of the International Searching Authority from corresponding International PCT Application No. PCT/US2009/055212 dated Oct. 15, 2009.

* cited by examiner

ARCH BARS FOR USE IN MAXILLOFACIAL SURGERY AND ORTHODONTICS

CROSS REFERENCE TO RELATED APPLICATION APPLICATIONS

This is the U.S. National Stage of International Application No. PCT/US2009/055212, filed Aug. 27, 2009, which was published in English under PCT Article 21(2), which in turn claims the benefit of U.S. Provisional Application No. 61/092,294, filed Aug. 27, 2008. The provisional application is incorporated herein in its entirety.

FIELD

The disclosure pertains to a system and method for intermaxillary fixation.

BACKGROUND

Repair of mandibular and maxillary fractures and osteotomies requires bringing the bone fragments into the proper position and alignment followed by temporary fixation of the upper and lower teeth in proper occlusion. Head and neck tumor reconstruction surgery also requires intermaxillary fixation to ensure proper alignment of the reconstructed jaws. Orthognathic surgery similarly requires maxillomandibular fixation that is typically achieved by using hooks the orthodontist attaches to arch wires. However, in orthognathic surgery, it is not uncommon for these brackets to loosen from the teeth and render them useless for intermaxillary fixation. Arch bars are often used in all the above circumstances to achieve intermaxillary fixation, but the arch bars are difficult to secure to the teeth, especially if the patients have pre-existing orthodontic appliances.

Arch bars are conventionally secured to the teeth by wires looped around the teeth or by direct bonding to the teeth, as disclosed in U.S. Pat. Nos. 3,474,779; 4,904,188; and 6,086,365. The front surfaces of the upper and lower arch bars typically have lugs or hooks, around which ligatures are applied to interconnect the upper and lower arch bars and provide fixation of the maxilla (upper jaw bone) and mandible (lower jaw bone). The dental arch bars disclosed in the prior art, however, are time-consuming to secure to the teeth and can cause puncture injuries to clinicians during installation, increasing the risk of disease transmission. Another disadvantage of such arch bars is that they may, depending on how many teeth are missing, not provide satisfactory fixation in an edentulous or partially edentulous patient. Moreover, circumdental wire fixation of arch bars to teeth requires anesthesia, is time consuming, and can cause periodontal injury to the patient.

An alternative to the dental arch bar is the direct placement of screws into the maxilla and mandible with ligatures used to interconnect the screws. For example, Synthes® offers an IMF Screw Set for temporary, perioperative stabilization of occlusion. A minimum of four screws are used, one on each side of the maxilla and one on each side of the mandible. The screws are placed superior to the maxillary tooth roots and inferior to the mandibular tooth roots, with care to also avoid the nerves within the maxilla and mandible. KLS Martin L. P. sells a similar fixation system in which 3-4 screws are placed in each of the maxilla and mandible and then interconnected with wire ligatures. These systems are contraindicated in patients with comminuted or displaced fractures. Further, these systems apply tension across discrete points rather than more evenly distributing tension across an extent of the maxilla and mandible. If the wires that traverse the jaws to provide maxillomandibular fixation stretch, the teeth can slide over one another and compromise the intermaxillary fixation. Additionally, because only several wires connect the maxillary screws to the mandibular screws, there is an uneven application of force providing the maxillomandibular fixation. In areas directly under the wire, premature contacts of the teeth may develop. In the areas between the intermaxillary wires, less pressure may result in regions where the teeth do not touch, producing an area of open bite.

Tellioğlu et al. (Eur. J. Plast. Surg., 1998, 21:215-216) disclose a method in which screws are placed directly into the maxilla, and an arch bar is placed over the screws and fastened with wires. A conventional arch bar is placed on the lower teeth without being attached by screws in the mandible. The arch bars are then interconnected with elastic ligatures. Gibbons et al. (British Journal of Oral and Maxillofacial Surgery, 2005, 43:365) disclose treatment of a fracture in a patient with two fixed bridges in the upper jaw using a dental arch bar secured by wires threaded through self-tapping screws placed in the alveolar bone of the maxilla. Because both of these described techniques use wires to secure the arch bar to the screws, mobility will occur as the wires undergo their normal tendency to stretch. The additional wiring takes time and exposes the clinician to the same puncture risk as conventional arch bars.

SUMMARY

Dental arch bars are disclosed that are capable of conforming to a dental arch of a subject. Ligature connectors project from the outer surface of the arch bar, and separate transverse arms extend from the arch bar. The transverse arms in some embodiments are movable relative to the arch bar and relative to each other so that the arms can be moved to position them between roots of the teeth. Fasteners can be placed through openings in the transverse arms to secure the arms to the subject's maxilla or mandible with the arch bar held against the corresponding dental arch, without having to attach the screws to wires. In some embodiments suitable for intermaxillary fixation, the dental arch bar system includes both an upper arch bar and a lower arch bar. In such embodiments, one or more ligatures are secured around the upper ligature connectors and the lower ligature connectors to achieve intermaxillary fixation. In particular embodiments, the ligature connectors are hooks or studs.

Methods of using the arch bar are also disclosed. For example, an inner surface of the arch bar is placed against the dental arch of a subject such that the arch bar conforms to the dental arch of the subject, and the transverse arms extend along a surface of the subject's maxilla or mandible. The transverse arms of the arch bar in some embodiments are moved and positioned between roots of the teeth before securing one or more transverse arms of the arch bar to the underlying bone with fasteners such as bone screws. In some embodiments, an inner surface of an upper arch bar is placed against the teeth of the upper dental arch with the transverse arms extending along an outer surface of the maxilla, and an inner surface of a lower dental arch bar is placed against the teeth of the lower dental arch with the transverse arms extending along an outer surface of the mandible. The transverse arms of the upper and lower arch bars are moved and positioned between roots of the upper and lower teeth before securing one or more transverse arms of the upper arch bar to the maxilla and one or more transverse arms of the lower arch bar to the mandible with fasteners. Ligatures then are secured around upper and lower ligature connectors to provide intermaxillary fixation.

In some embodiments of the method, a single dental arch bar is utilized. If the arch bar has been placed against the upper dental arch, one or more opposing ligature connectors (such as bone screws) are placed directly in the mandible without being associated with an arch bar. If the arch bar has been placed against the lower dental arch, one or more opposing ligature connectors (such as bone screws) are placed directly in the maxilla. Ligatures then are secured around one or more arch bar ligature connectors and one or more opposing ligature connectors, such that intermaxillary fixation is achieved.

In other embodiments, a dental arch bar includes a longitudinally extending member capable of conforming to a dental arch of a subject. The longitudinally extending member has a plurality of fastener openings and a plurality of ligature connectors, with the fastener openings and ligature connectors being spaced apart from one another along a main axis of the longitudinally extending member. The fastener openings can be configured to receive a fastener for securing the dental arch bar to a maxilla at a location between adjacent roots of the maxillary teeth or to a mandible at a location between adjacent roots of the mandibular teeth.

In some embodiments, the ligature connectors comprise a plurality of hook members. In others, the ligature connectors comprise a plurality of projections, with each projection having an aperture extending through a portion of the projection and sized to receive a ligature. In other embodiments, the longitudinally extending member has a front surface and an inner surface, and the longitudinally extending member further has one or more spacer members that extend from the inner surface of the longitudinally extending member. In some embodiments, the spacer members extend from the inner surface at or adjacent to one or more fastener openings and are configured to space the inner surface of the longitudinally extending member from mucosal tissue when the longitudinally extending member is secured to the maxilla or the mandible.

In other embodiments, a dental arch bar has a longitudinally extending member and a connecting member. The longitudinally extending member can have a plurality of fastener openings spaced apart along a main axis of the longitudinally extending member. The connecting member can extend from an occlusal side of the longitudinally extending member. The connecting member can have a first portion that extends outward from the occlusal side and a second portion that extends at an angle substantially perpendicular to the first portion. The fastener openings can be configured to receive a fastener for securing the longitudinally extending member to a maxilla at a location between adjacent roots of the maxillary teeth. The second portion of the connecting member can be configured to be coupled to an external fixation device. In some embodiments, the connecting member is integrally formed with the longitudinally extending member and/or substantially L-shaped. In other embodiments, the connecting member can be connected to an internal fixation device.

In another embodiment, another method for performing intermaxillary fixation in a subject is provided. The method includes providing an elongated upper and lower arch bar capable of conforming to an upper and lower dental arch, respectively. The upper and lower arch bars have a plurality of upper and lower fastener openings and a plurality of upper and lower ligature connectors spaced apart from one another along a main axis of the upper and lower arch bars, respectively. The method further includes placing an inner surface of the upper arch bar against the upper dental arch with the upper arch bar conforming to the upper dental arch of the subject such that two or more upper fastener openings are positioned adjacent a maxilla of the subject at a location between adjacent roots of maxillary teeth; securing the upper arch bar to the maxilla by inserting a fastener through two or more upper fastener openings of the upper arch bar; placing an inner surface of the lower arch bar against the lower dental arch with the lower arch bar conforming to the lower dental arch of the subject such that two or more lower fastener openings of the elongated lower arch bar are positioned adjacent a mandible of the subject at a between adjacent roots of mandibular teeth; securing the lower arch bar to the mandible by inserting a fastener through two or more lower fastener openings of the lower arch bar; and securing one or more upper and lower ligature connectors to one another to perform intermaxillary fixation of the subject.

In some embodiments, the upper ligature connectors project from an outer surface of the upper arch bar and the lower ligature connectors project from an outer surface of the lower arch bar. The ligature connectors can have hooks or studs. In some embodiments, the upper arch bar has at least four upper fastener openings, and the lower arch bar has at least four lower fastener openings.

In another embodiment, a method for adjusting or modifying the forces applied by an orthodontic device to the teeth of a subject is provided. The method includes providing an elongated upper arch bar capable of conforming to an upper dental arch. The upper arch bar has a plurality of upper fastener openings and a plurality of upper ligature connectors, with the upper fastener openings and upper ligature connectors being spaced apart from one another along a main axis of the upper arch bar. The method further includes: placing an inner surface of the upper arch bar against the upper dental arch with the upper arch bar conforming to the upper dental arch of the subject such that two or more upper fastener openings are positioned adjacent a maxilla of the subject at a location between adjacent roots of maxillary teeth; securing the upper arch bar to the maxilla by inserting a fastener through two or more upper fastener openings of the upper arch bar; and securing one or more upper ligature connectors to a portion of the orthodontic device with one or more ligatures to adjust or modify a force exerted on the maxillary teeth by the orthodontic device.

In some embodiments, an elongated lower arch bar capable of conforming to a lower dental arch is provided. The lower arch bar has a plurality of lower fastener openings and a plurality of lower ligature connectors. The lower fastener openings and lower ligature connectors are spaced apart from one another along a main axis of the lower arch bar. The method further includes: placing an inner surface of the lower arch bar against the lower dental arch with the lower arch bar conforming to the lower dental arch of the subject such that two or more lower fastener openings of the elongated lower arch bar are positioned adjacent a mandible of the subject at a location between adjacent roots of mandibular teeth; securing the lower arch bar to the mandible by inserting a fastener through two or more lower fastener openings of the lower arch bar; and securing one or more lower ligature connectors to a portion of the orthodontic device with one or more ligatures to adjust or modify a force exerted on the mandibular teeth by the orthodontic device.

In some embodiments, the upper ligature connectors project from an outer surface of the upper arch bar and the lower ligature connectors project from an outer surface of the lower arch bar. The ligature connectors can include hooks or studs. In some embodiments, the upper arch bar has at least four upper fastener openings, and the lower arch bar has at least four lower fastener openings.

In another embodiment, a method for distracting a maxilla of a subject is provided. The method includes providing an elongated upper arch bar capable of conforming to an upper dental arch. The elongated upper arch bar has a plurality of fastener openings spaced apart along a main axis of the upper arch bar. The method further comprises: placing an inner surface of the upper arch bar against the upper dental arch with the upper arch bar conforming to the upper dental arch of the subject such that two or more upper fastener openings are positioned adjacent a maxilla of the subject at a location between adjacent roots of maxillary teeth; securing the upper arch bar to the maxilla by inserting a fastener through two or more upper fastener openings of the upper arch bar; providing a connecting member extending from an occlusal side of the upper arch bar; providing an external or internal fixation device; and securing the connecting member to the external or internal fixation device to exert a force on the maxilla. The connecting member can have a first portion that extends outward from the occlusal side and a second portion that extends at an angle substantially perpendicular to the first portion.

In another embodiment, an elongated arch bar can be fastened to the mandible at a location between adjacent roots of mandibular teeth, and the connecting member can be secured to an external or internal fixation device to exert a force on the mandible.

The foregoing and other objects, features, and advantages of the invention will become more apparent from the following detailed description, which proceeds with reference to the accompanying figures.

DETAILED DESCRIPTION

The following description is exemplary in nature and is not intended to limit the scope, applicability, or configuration of the invention in any way. Various changes to the described embodiment may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed if possible.

Moreover, for the sake of simplicity, the attached figures may not show the various ways (readily discernable, based on this disclosure, by one of ordinary skill in the art) in which the disclosed system, method, and apparatus can be used in combination with other systems, methods, and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

Figure 1:
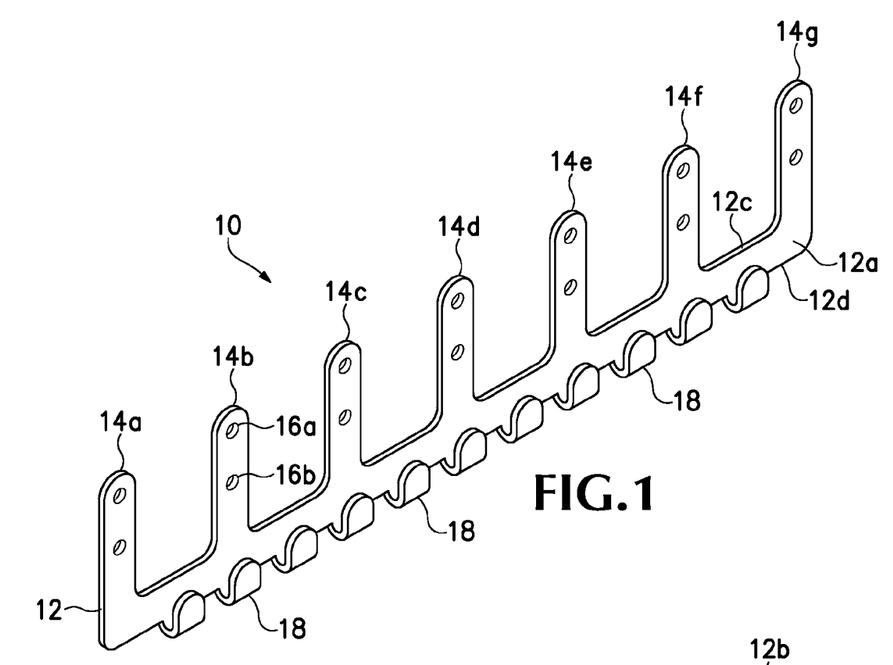
FIG. 1 is a front perspective view of an embodiment of a dental arch bar.
Figure 2:
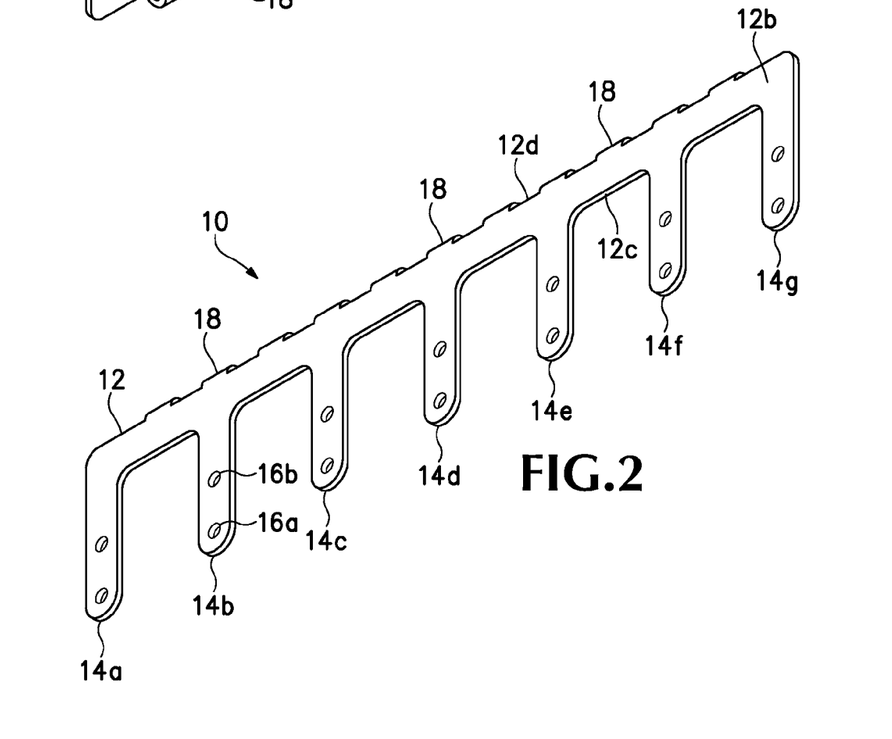
FIG. 2 is a rear perspective view of the dental arch bar of FIG. 1.

A system and method for intermaxillary fixation is disclosed herein. FIGS. 1 and 2 illustrate a first embodiment of a dental arch bar system 10. The system 10 includes an elongated, substantially rectangular dental arch bar 12 capable of conforming to a dental arch of a subject. The dental arch is the curved structure formed by the natural dentition. The upper teeth form the upper dental arch and the lower teeth form the lower dental arch.

Arch bar 12 is made of any suitable material capable of conforming to the dental arch, and it is of sufficient length to extend over at least 5 or 6 teeth of the dental arch to which it is to be applied. For example, it may be about 1 to 20 cm in length, and in some embodiments is 4 to 8 cm in length. Arch bar 12 has an outer surface 12a, an inner surface 12b, a gingival edge 12c and an occlusal edge 12d. Arch bar 12 can be manufactured from a metal or a plastic material that is sufficiently malleable to allow it to flex from a flat shape to a curved configuration that is capable of conforming to a dental arch with inner surface 12b abutting the buccal aspect of the underlying teeth. However the malleable material retains a sufficiently rigid shape to allow its use in intermaxillary fixation. For the purposes of this disclosure, the term malleable means pliable, flexible, or otherwise capable of being shaped or bent, and includes resilient and non-resilient materials.

Dental arch bar 12 includes a plurality of separate, spaced transverse arms 14 projecting from gingival edge 12*c* of arch bar 12. In the illustrated embodiment of FIG. 1, six arms 14*a*, 14*b*, 14*c*, 14*d*, 14*e* and 14*f* (collectively referred to as "arms 14") extend from arch bar 12. Each of arms 14 is a generally rectangular extension that extends generally transverse from gingival edge 12*c* of arch bar 12 a distance of about 2-4 cm to a tip with a curved edge, which is a sufficient distance to extend from the surface of a tooth across the gingival margin and along a surface of the mucosa that covers the mandible or maxilla to which the dental arch is attached. Each of arms 14 is separate from any of the other arms, such that each arm is movable relative to arch bar 12 and relative to the other arms. For example, arms 14 are movable from a position in which arms 14 are substantially parallel to one another (as in FIGS. 1-2) to positions in which one or more of arms 14 are not substantially parallel to one or more of the other arms 14. In particular embodiments, arms 14 are constructed of a malleable material such that the transverse arms 14 can be moved by bending them. For example, the connection between each arm 14 and arch bar 12 is sufficiently malleable that each arm is capable of flexing in angular movement relative to arch bar 12. The angular movement can be in all directions (x, y and z movement) relative to a pivot point at the connection between arch bar 12 and arm 14; however the preferred movement is generally x-y movement in a frontal plane relative to fixed arch bar 12. Although malleable arms are depicted in FIGS. 1-4, other embodiments of movable arms 14 are envisioned, such as hinged arms that are interconnected to arch bar 12 by a hinge means that selectively permits arms 14 to move in the desired directions relative to a fixed point at the connection of arch bar 12 to each of arms 14. The hinge can be tightened when an arm reaches a desired angular position to fix the arm in a desired position.

Each arm 14 has at least one fastener opening 16 that extends completely through the transverse arm 14. In the depicted embodiment, each arm 14 has two round openings 16*a* and 16*b* which are dimensioned to receive a bone screw. Openings 16*a* and 16*b* are respectively spaced distally and proximally along each of arms 16, with distal opening 16*a* being positioned near a terminus of each arm 14 and proximal opening 16*b* positioned intermediate distal opening 16*a* and the junction of arm 14 with the body of arch bar 12.

A series of ligature connectors 18 extend outwardly from outer surface 12*a* of arch bar 12. In the particularly depicted embodiment, each connector 18 forms a generally J-shaped hook-like member with a curved first portion that originates at occlusal edge 12*d* of arch bar 12 and extends away from front surface 12*a*, and a second portion that extends generally parallel to front surface 12*a* toward gingival edge 12*c* of arch bar 12. Each connector 18 terminates in a rounded tip that is spaced away from the front of arch bar 12, approximately half-way between gingival and occlusal edges 12*c*, 12*d*. In the illustrated embodiment of FIGS. 1-4, connectors 18 are formed as an integral part of the arch bar 12. In other embodiments, the connectors 18 are formed separately and then secured by any suitable method to arch bar 12.

Figure 3:
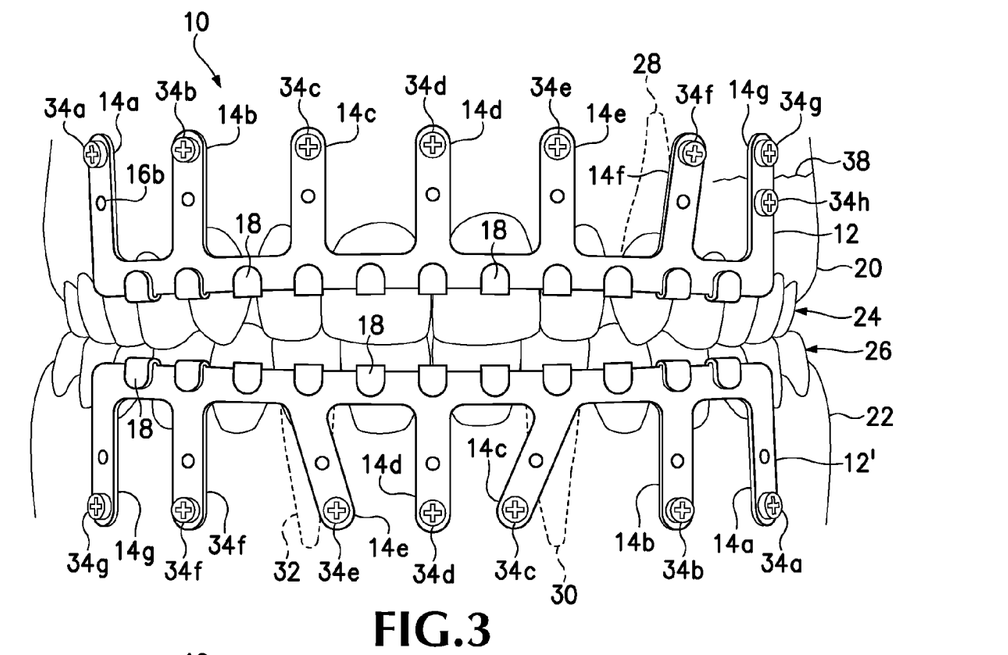
FIG. 3 is a front elevational view of an upper dental arch bar of FIG. 1 fastened to a maxilla and a lower dental arch bar of FIG. 1 fastened to a mandible.
Figure 4:
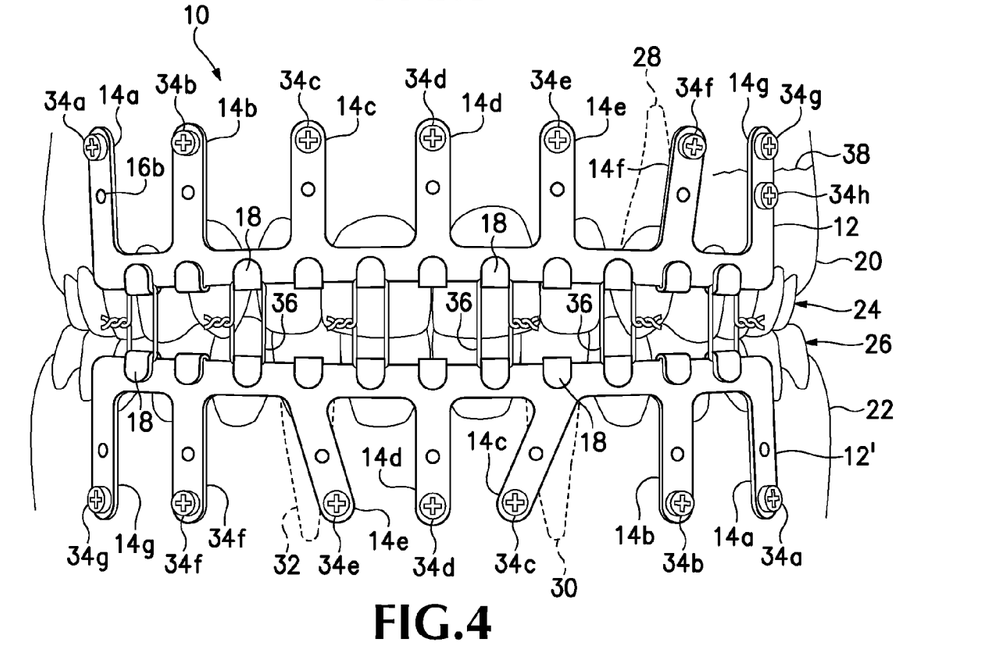
FIG. 4 is a front elevational view of the dental arch bars of FIG. 3 with ligatures connecting the upper and lower dental arch bars.

In use, as shown in FIGS. 3 and 4, dental arch bar system 10 is applied to the dental arches of a subject who is in need of intermaxillary fixation with relative immobilization of the maxilla and mandible relative to one another. An example of such a subject is someone who has a fracture of the maxilla 20 or mandible 22, and in whom motion of the affected bone should be minimized to promote healing of the fracture. Appropriate anesthesia is optionally provided, for example by a local block of the affected tissue or while a patient is under general anesthesia (for example, following surgical repair of the fracture but before general anesthesia is reversed). An arch bar 12 is then placed against the teeth of each of upper dental arch 24 and lower dental arch 26 (where the upper arch bar in FIGS. 3 and 4 is designated arch bar 12 and the lower arch bar is designated arch bar 12'). Arch bars 12, 12' are identical to one another, except arch bar 12' is inverted relative to arch bar 12 so that it can be applied to the lower dental arch. The arch bars 12, 12' are positioned with inner surface 12*b* of each arch bar 12, 12' placed against the buccal (outer) surfaces of the teeth, with arch bars 12, 12' being sufficiently malleable to conform to the curve of the upper and lower dental arches against which each arch bar 12, 12' is respectively applied. The arch bars placed against the upper and lower dental arches are also generally aligned so that connectors 18 of the upper arch bar 12 are generally vertically aligned above connectors 18 of the lower arch bar 12' when the jaw is in the position in which fixation is to be achieved.

Arms 14 from each arch bar are positioned generally between the roots 28 of the teeth (one of which is shown in phantom in FIGS. 3 and 4, although it is understood that each of the teeth has a corresponding root, the path of which can generally be discerned from the overlying external anatomy). For any arm that does not align between the apparent pathway of a root, the corresponding arm 14 can be gently deformed to move it away from the root pathway. This feature is illustrated in FIG. 3, wherein arm 14*f* of upper arch bar 12 is slightly moved away from underlying root 28 of an incisor of upper dental arch 24 so that distal opening 16*a* is not positioned over root 28. Similarly, arms 14*c* and 14*e* of lower arch bar 12' on lower dental arch 26 are angled away from their transverse position to avoid underlying roots 30 and 32.

Surgical screws 34 are then introduced through one or both of openings 16*a*, 16*b* in arms 14 to affix each arch bar 12, 12' to its respective dental arch. In the embodiment shown in FIG. 3, a surgical screw 34*a*, 34*b*, 34*c*, 34*d*, 34*e*, 34*f* or 34*g* (collectively referred to as screws 34) is introduced only through distal opening 16*a* (not visible in FIGS. 3-4) of each of arms 14*a*, 14*b*, 14*c*, 14*d*, 14*e*, 14*f* or 14*g*, and advanced into the underlying bone of maxilla 20 or mandible 22. The choice of whether to use distal opening 16*a* or proximal opening 16*b* may depend on the anatomy of the patient and the placement of arch bar 12 on the dental arch. Similarly, screws 34 can be introduced through both of openings 16*a*, 16*b* to more securely affix arch bar 12 to its respective dental arch. Holes 16*a* and 16*b* can also be used to approximate fracture segments and align them into proper position in multi-piece or comminuted fractures. For example, as shown in FIGS. 3-4, two screws 34*g*, 34*h* on opposing sides of a fracture 38 can be placed through two holes on the same arm 14*g* to help secure the fractured segments of bone to one another. Using these holes to fix screws to bone segments makes the ultimate adaptation of the reconstruction plate easier and faster.

Optionally, arch bars 12, 12' can be further secured to the surfaces of the teeth using an adhesive prior to attaching the arms to the bone using the bone screws. However, this additional step is usually unnecessary in view of the stable fixation of arch bars 12, 12' using the bone screws through the multiple arms 14.

Once the arch bars have been secured with screws 34 to their respective upper and lower dental arches 24, 26, intermaxillary fixation is performed by placing ligatures around corresponding pairs of connectors 18. For example, as shown in FIG. 4, a surgical fastener wire 36 is wrapped around opposing pairs of generally vertically aligned connectors 18 and secured to itself by twisting the ends of the wire 36 around each other. The ligatures can be provided on only a subset of opposing pairs of connectors (as shown in FIG. 4 wherein only every other pair of connectors is fixed to one another) or secured around more than half or all of the opposing pair of connectors to achieve greater fixation. As an alternative, the ligatures can be, for example, plastic loops, elastomeric members (such as elastic bands), or combinations thereof. One of ordinary skill in the art will appreciate that other suitable ligatures can be used.

Figure 5:
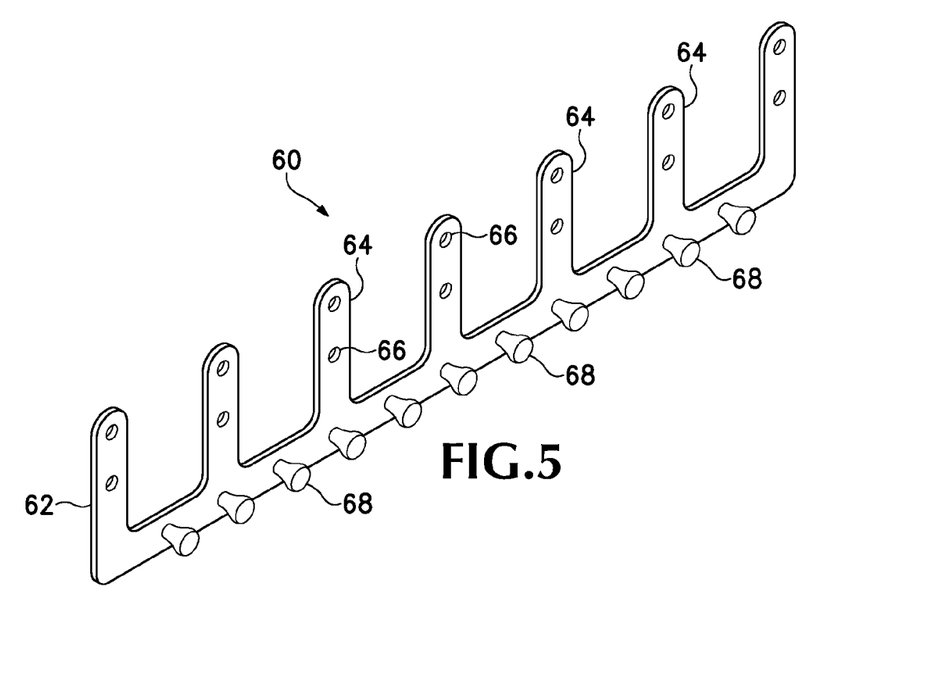
FIG. 5 is a front perspective view of an embodiment of a dental arch bar.

Another embodiment of a dental arch bar system 60 is illustrated in FIG. 5, which is generally similar to the arch bar embodiment of FIGS. 1-4 except for the specific configuration of the connectors as described in greater detail below. The arch bar system 60 includes a dental arch bar 62 capable of conforming to a dental arch of a subject. When utilized, arch bar 62 is bent such that it conforms to the subject's dental arch. Arch bar 62 is made of any suitable material capable of conforming to the dental arch. For example, arch bar 62 can be manufactured from a metal or a plastic that is malleable or capable of conforming to a desired shape. Arch bar 62 includes a plurality of separate transverse arms 64 projecting from arch bar 62. Arms 64 are movable relative to arch bar 62 and relative to each other. In particular embodiments, arms 64 are constructed of a malleable material such arms 64 can be moved by bending them. Each of arms 64 has at least one fastener opening 66 through arm 64. Arch bar 62 further includes a plurality of ligature connectors 68 that project outwardly from arch bar 62. In the embodiment shown in FIG. 5, the ligature connectors 68 are studs. The studs 68 are somewhat frustoconical and have a diameter that tapers inwardly from an enlarged distal end of stud 68 to the body of arch bar 62. The studs 68 can be formed as an integral part of arch bar 62. Alternatively, studs 68 can be formed separately and then securely attached by any suitable method to arch bar 62.

Figure 6:
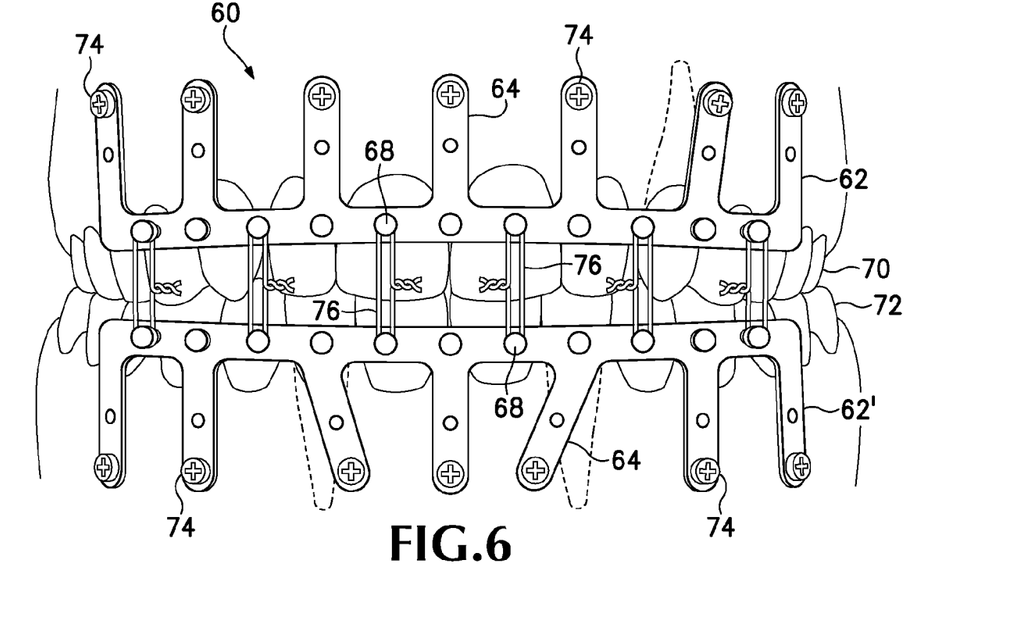
FIG. 6 is a front elevational view of two dental arch bars of FIG. 5 fastened to a maxilla and a mandible, with ligatures connecting the upper and lower dental arch bar.

In use, a first arch bar 62 is placed against the upper dental arch 70 and a second arch bar 62' is placed against the lower dental arch 72, as shown in FIG. 6. Arch bars 62, 62' are secured to upper and lower dental arches by introducing surgical screws 74 through openings 66 in the arch bars, as already described in connection with the embodiment of FIGS. 1-4. Upper and lower arch bars are generally positioned so that studs 68 of the upper arch bar 62 are generally vertically aligned with studs 68 of the lower arch bar 62'. Connectors 68 are secured to one another using ligatures 76, similarly to the method of intermaxillary fixation described above in connection with FIGS. 1-4.

In some other alternative embodiments (not illustrated), a single dental arch bar is utilized. For example, a lower arch bar can be used if a subject has a fractured mandible. Alternatively, an upper arch bar can be used if a subject has a fractured maxilla. The opposing ligature connectors can be any suitable connectors capable of being directly secured to the maxilla or mandible. For example, the opposing ligature connectors can be screws that are secured directly in the bone of the opposing mandible or maxilla. After secure placement of the dental arch bar and the opposing ligature connectors, one or more ligatures are secured around one or more arch bar ligature connectors and one or more opposing ligature connectors, such that intermaxillary fixation is achieved.

The arch bar system therefore includes any single unit device that attaches directly to bone, either buried under mucosa or transmucosally, that is used to provide intermaxillary fixation by having separate wires, elastics, or other methods of fixation that secure the maxillary screw-anchored bar to the mandibular screw-anchored bar. It also includes any device that is secured to the maxilla and mandible as separate units, but the screw-anchored bars themselves can be manipulated to attach to each other to eliminate the step of a wire loop or elastic that connects the maxillary device to the mandibular device (not illustrated). For example, the connectors on each arch bar can connect directly to one another instead of being indirectly interconnected by the ligatures. In such an embodiment, the upper and lower connectors are complementary members that are selectively locked to one another to achieve fixation.

Figure 7:
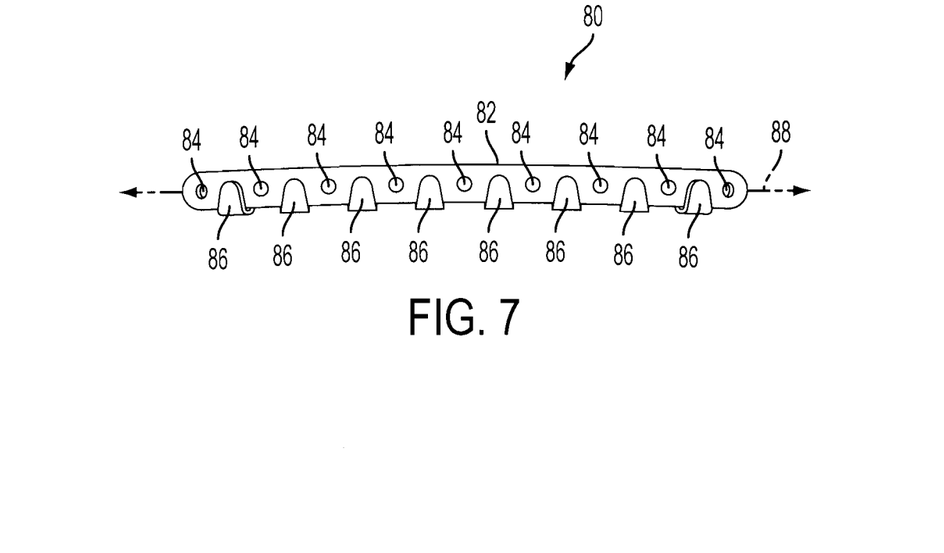
FIG. 7 is a front elevational view of an embodiment of a dental arch bar.

In another embodiment, another arch bar system is provided for use in intermaxillary fixation procedures. FIG. 7 illustrates an arch bar system 80, which includes a dental arch bar 82 capable of conforming to a dental arch of a subject. When utilized, arch bar 82 is bent such that it substantially conforms to the subject's dental arch. As with the other arch bars disclosed herein, arch bar 82 can be made of any suitable material capable of conforming to the dental arch, such as a metal or a plastic that is malleable or capable of conforming to a desired shape.

Arch bar 82 comprises a plurality of fastener openings 84 and a plurality of ligature connectors 86. Each of the plurality of fastener openings 84 is sized to receive a surgical screw, and each of the plurality of ligature connectors 86 projects outward from the arch bar 82 to receive one or more ligatures. In the embodiment shown in FIG. 7, ligature connectors 86 are hook members. The hook members can taper to a narrower width at a far end (i.e., the end furthest from the arch bar) as shown in FIG. 7. Alternatively, the hook member can take other shapes. For example, it can narrow at a middle portion and then get wider at the far end to further secure a ligature to the hook member. In addition, it should be understood that other configurations of ligature connectors can be used in connection with arch bar 82, including, for example, the other ligature connectors described herein.

Unlike the embodiments shown in FIGS. 1-6, arch bar 82 lacks the transverse arms that project from the bodies of the arch bar of FIGS. 1-6. Instead, arch bar 82 is configured so that the fastener openings 84 and ligature connectors 86 are substantially located along the same axis of the arch bar 82. That is, as shown in FIG. 7, the fastener openings 84 and the ligature connectors 86 are positioned along a longitudinal axis 88 of arch bar 82, substantially in-line with one another. By eliminating the transverse arms of other embodiments, arch bar 82 achieves a lower profile that can be simpler for the orthodontist to fix in place and less cumbersome or uncomfortable for the patient to wear. In addition, because there are a plurality of fastener openings along the main axis of the arch bar 82, the arch bar can be positioned lower on the upper dental arch (or higher on the lower dental arch). That is, because the arch bar has a number of fastener openings spaced apart along the arch bar, in most cases the arch bar can be positioned within the tooth roots of the upper or lower dental arch, and a plurality of the fastener openings will fall between tooth roots. Thus, the fastener openings that fall between adjacent tooth roots can receive a fastener to secure the arch bar to the maxilla or mandible without impacting the tooth roots.

Figure 8:
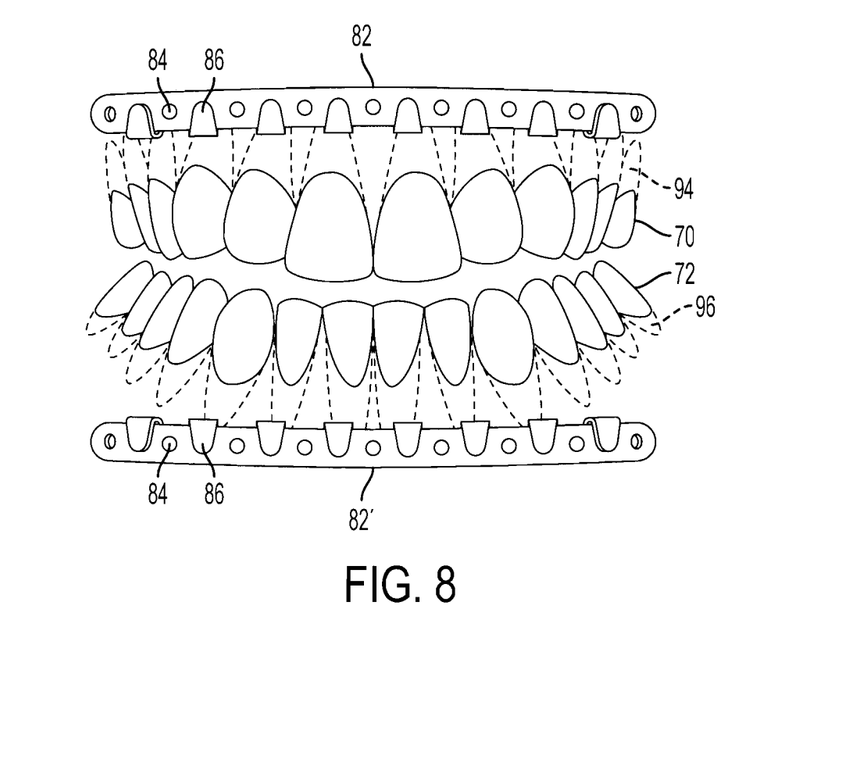
FIG. 8 is a front elevational view of an upper dental arch bar of FIG. 7 fastened to a maxilla and a lower dental arch bar of FIG. 7 fastened to a mandible.
Figure 9:
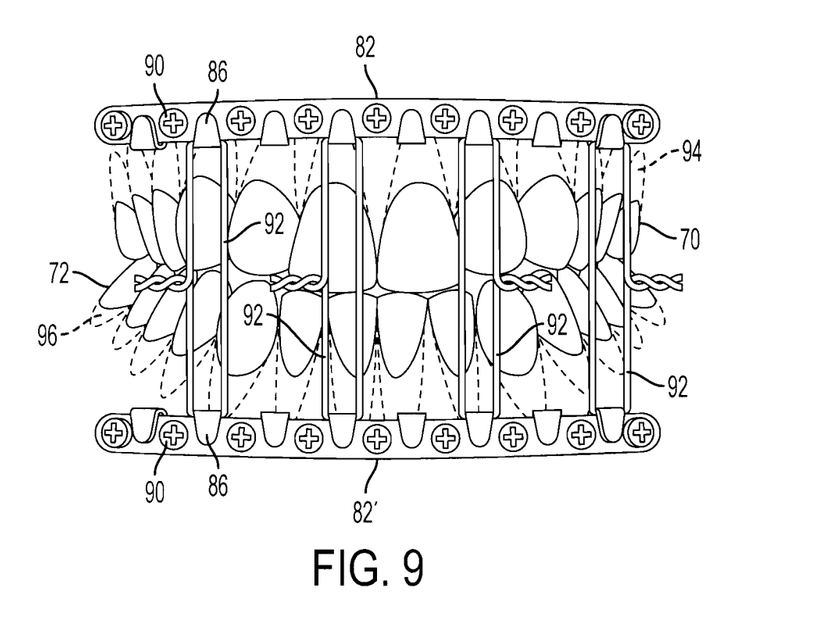
FIG. 9 is a front elevational view of the dental arch bars of FIG. 8 with ligatures connecting the upper and lower dental arch bars.

Referring to FIGS. 8 and 9, a method for performing intermaxillary fixation on a patient is described. A first arch bar 82 is placed against the upper dental arch 70 and a second arch bar 82' is placed against the lower dental arch 72, as shown in FIG. 8. Second arch bar 82' can be substantially identically to first arch bar 82, but rotated 180 degrees or otherwise inverted to conform to the lower dental arch as shown in FIG. 8. Arch bars 82, 82' can be secured to upper and lower dental arches by introducing surgical screws 90 through fastener openings 84 in the arch bars 82, 82'. Upper and lower arch bars 82, 82' are preferably positioned so that ligature connectors 86 of the upper arch bar 82 are generally vertically aligned with ligature connectors 86 of the lower arch bar 82'. Ligature connectors 86 are secured to one another using ligatures 92 in a manner similar to that which is described above in connection with FIGS. 1-6.

Referring to FIGS. 8 and 9, surgical screws 90 are introduced through openings 84 into the underlying bone of maxilla 20 or mandible 22. As discussed above, to avoid impacting underlying roots, arch bars 82, 82' are preferably positioned so that at least some of the fastener openings 84 are located away from (e.g., in between) maxillary tooth roots 94 or mandibular tooth roots 96. Since arch bars 82, 82' are provided with a plurality of fastener openings, the orthodontist can secure the arch bars at multiple locations to ensure that the arch bars are firmly held in position during the fixation procedure and throughout the desired period of fixation. Also, because of the number of potential fastener openings to choose from, the orthodontist can secure fasteners through the fastener openings that are located between tooth roots.

The arch bars 82, 82' are preferably positioned as close together as possible to maximize the ability of the arch bars to stabilize the movement of the teeth and jaw. Referring to FIGS. 8 and 9, the arch bars can be moved further apart than shown; however, if they are moved too far apart, the stability of the fixation procedure may be lessened. On the other hand, the device will be easier to secure without impacting any roots of the maxillary or mandibular teeth. The arch bars can also be moved closer together than shown in FIGS. 8 and 9. The arch bars are preferably not moved too close together that a plurality of fastener openings are not located between adjacent roots of maxillary or mandibular teeth to provide anchorage locations to fix the arch bars to the maxilla or mandible.

Preferably, each of the lower and upper arch bars have at least 3 fastener openings, more preferably at least 4 fastener openings, more preferably at least 5 fastener openings, and even more preferably at least 6 openings. By providing a plurality of fastener openings along an arch bar as described herein, fastener openings that fall between roots of maxillary and mandibular teeth can be more easily located and used to secure the arch bars to the maxilla or mandible. It should be understood that the fixation of each arch bar can be achieved by securing surgical screws through less than all of the fastener openings that are provided on that arch bar. However, to firmly secure the arch bars to the maxilla or mandible, preferably at least two or more fasteners are secured through fastener openings.

Figure 10:
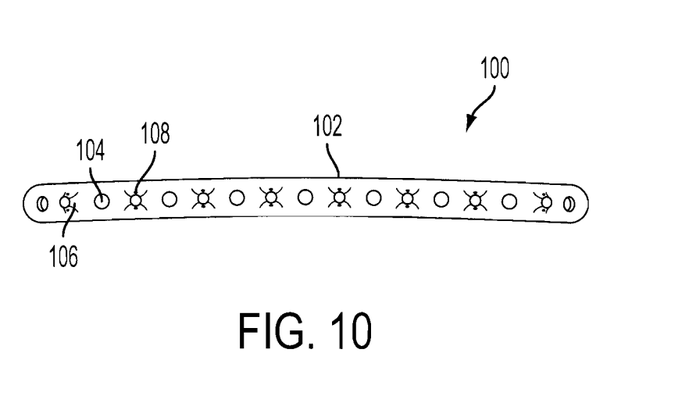
FIG. 10 is a front elevational view of an embodiment of a dental arch bar.

In another embodiment, another arch bar system is provided for use in intermaxillary fixation procedures. FIG. 10 illustrates an arch bar system 100, which includes a dental arch bar 102 capable of conforming to a dental arch of a subject. Arch bar 102 is substantially similar to arch bar 82, which is shown in FIG. 7 and described in detail above.

Like arch bar 82, arch bar 102 comprises a plurality of fastener openings 104 and a plurality of ligature connectors 106. Each of the plurality of fastener openings 104 is sized to receive a surgical screw, and each of the plurality of ligature connectors 106 projects outward from the arch bar 102 to receive one or more ligatures. Arch bar 82 differs from arch bar 102 in that ligature connectors 106 are projections that comprise an aperture 108 for receiving a ligature (e.g., a wire or other connecting means). As will be readily understood, a ligature can be passed through the aperture to secure (tie) the ligature to a ligature connector 106. Although the ligature connectors 106 are shown as cone-shaped (e.g., frustoconical) members with an aperture in FIGS. 10-12, it should be understood that other shapes or configurations can be used to provide anchorage support locations for a ligature or other connecting means.

Arch bar 102 can be used in the same manner as arch bar 82, discussed above. For example, a first arch bar 102 can be secured to the upper dental arch 70 and a second, substantially identical but inverted, arch bar can be secured to the lower dental arch 72. Ligatures (e.g., wires) can secure portions of the first and second arch by, for example, passing a wire through the apertures 108 of the ligature connectors 106 and securing opposing, substantially vertically aligned, ligature connectors 106 in a manner similar to that shown in FIG. 9.

In another embodiment, the arch bars shown in FIGS. 7 and 10 can be used in combination with orthodontic devices, such as orthodontic braces. For example, as shown in FIG. 11, a first arch bar 102 can be secured to the upper dental arch 70 and a second, substantially identical but inverted, arch bar 102' can be secured to the lower dental arch 72 in the manner described above.

For convenience, fastener openings 104 are shown without surgical screws (or other fasteners) extending therethrough to secure the arch bars 102, 102' to the maxilla and mandible, respectively. However, it should be understood that the method of securing the arch bars in this embodiment can be the same or similar to the methods disclosed in other embodiments, such as, for example, by using surgical screws as shown in FIG. 3. Also, although shown herein with two opposing arch bars provided, it should be understood that both arch bars need not be installed; that is, only the first arch bar 102 could be secured to the upper dental arch or only the second arch bar 102' could be secured to the lower dental arch.

Figure 11:
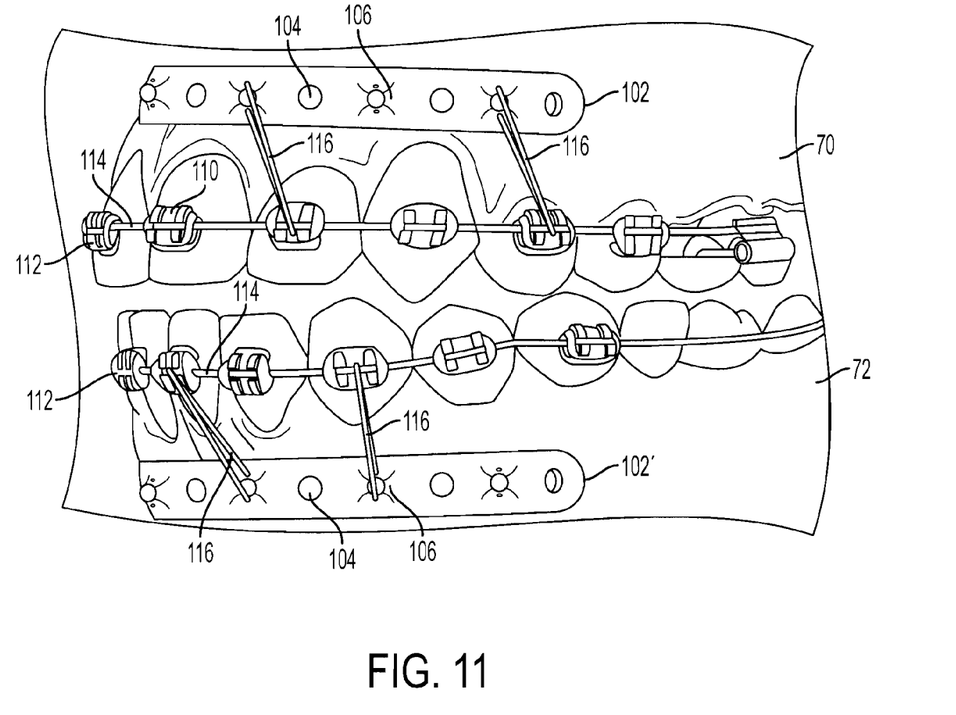
FIG. 11 is a side elevational view of an upper dental arch bar of FIG. 10 fastened to a maxilla and a lower dental arch bar of FIG. 10 fastened to a mandible, with ligatures connecting the dental arch bars with portions of orthodontic braces.

The orthodontic braces 110 shown in FIG. 11 can be secured to the patient's teeth in any conventional manner. Orthodontic braces 110 can comprise, for example, a plurality of brackets 112 coupled to teeth and a plurality of arch wires 114 extending between brackets 112. As is well known, orthodontic braces can be used to correct malocclusions, such as underbites, overbites, cross bites, and/or other structural or cosmetic flaws of the teeth and jaws. The arch bars described herein can be used to correct and/or supplement the forces being applied on the teeth and jaws by the braces.

For example, as shown in FIG. 11, one end of a ligature (e.g., a wire) 116 can be secured to a portion of the orthodontic braces 110 (such as a bracket 112) and the other end can be secured to a ligature connector 106. Ligature 116 can be secured to the ligature connector 106 by, for example, passing the ligature through the aperture 108 of the ligature connector 106. The ligature can be tied or locked in that position by any conventional means. A desired force can be applied to the jaw or teeth by adjusting the tension of each secured ligature 116. Thus, as shown in FIG. 11, arch bars 102, 102' can be provided to provide additional anchoring locations from which ligatures can apply forces to the orthodontic braces, teeth, and/or jaw.

Over time, direct contact of the arch bar with the mucosal tissue may cause or contribute to various possible hygiene problems. Accordingly, to reduce such potential problems, in another embodiment, a spacer can be provided to space the arch bar away from the mucosal tissue that overlays the jaws. Although such spacers can be used in connection with any of the arch bar embodiments discussed herein, it can be particularly useful when the arch bars are intended to be secured within to the maxilla and/or mandible for a long duration of time. For example, when arch bars are used in connection with maxillomandibular fixation, the arch bars will generally be secured within the mouth for a period of a few weeks.

Thus, although the spacing of the arch bars from the mucosal tissue can still be helpful, it may not be as helpful as when the arch bars are fixed within the mouth for a longer period of time. For example, when arch bars are used in connection with orthodontic braces, it can be desirable to leave the arch bars in for a much longer time period (e.g., greater than two weeks, such as, for example, one month or longer). For such longer duration uses, it can be particularly useful to prevent the arch bars from continual contact with the muscosal tissue.

Figure 12:
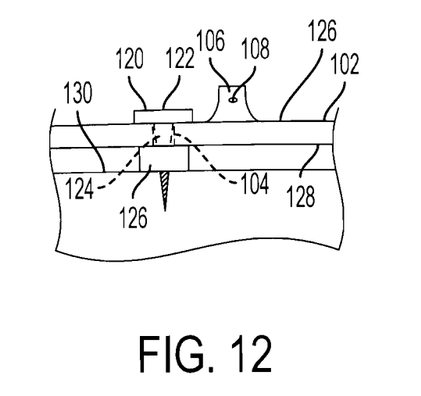
FIG. 12 is a cross-sectional view of a portion of a dental arch bar fixed to a maxilla or mandible of a patient, shown with a spacer member positioned between the dental arch bar and mucosal tissue.

FIG. 12 illustrates a cross sectional view of a portion of an arch bar 102 for fixation to a maxilla and/or mandible in such a manner that the arch bar is substantially prevented from contacting the muscosal tissue of the jaw.

As shown in FIG. 12, a surgical screw 120 has a screw head 122 that is greater in diameter than the diameter of the fastener opening 104, and a screw body 124 that is smaller in diameter than diameter of the fastener opening. The arch bar 102 comprises a front side 126 and an inner surface 128. Inner surface 128 faces the muscosal tissue of a patient when the arch bar is secured to the maxilla and/or mandible of the patient. A spacer member 126 is configured to be positioned on inner surface 128 of the arch bar 102 to space the arch bar 102 from the muscosal tissue 130. Preferably, the spacer member has a thickness (or depth) of about 1 mm, more preferably about 2 mm, or more preferably about 3 mm. Thus, the distance between arch bar 102, when secured to the maxilla or mandible, is preferably greater than 1 mm. Of course, surgical screw 120 preferably has a length that is sufficient to extend beyond the thickness of spacer member 126 far enough to secure the arch bar 102 to the maxilla or mandible.

Spacer member 102 can be formed integral to the arch bar 102 or it can be a separate member. However, it is preferable that it is formed integral to the arch bar 102 to facilitate securing the arch bar 102 to the maxilla or mandible.

Figure 13:
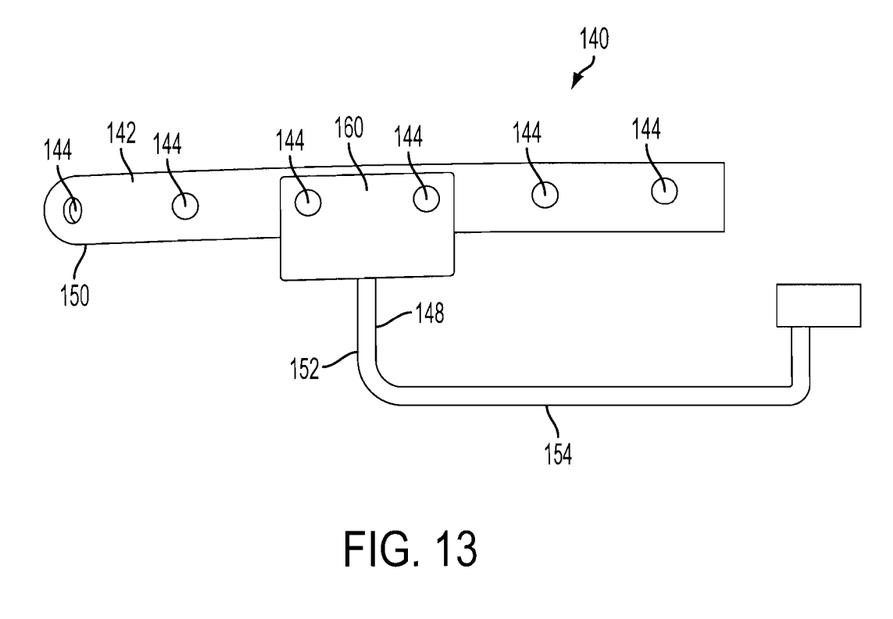
FIG. 13 is a view of an embodiment of an arch bar that comprises a connecting member.

FIG. 13 illustrates another embodiment of an arch bar that can be secured to a portion of a jaw. Arch bar system 140 comprises an arch bar 142 that has a plurality of fastener openings 144. Each of the plurality of fastener openings 84 is sized to receive a surgical screw to secure the arch bar 142 to the maxilla in the same general manner as described above in other embodiments.

Figure 14:
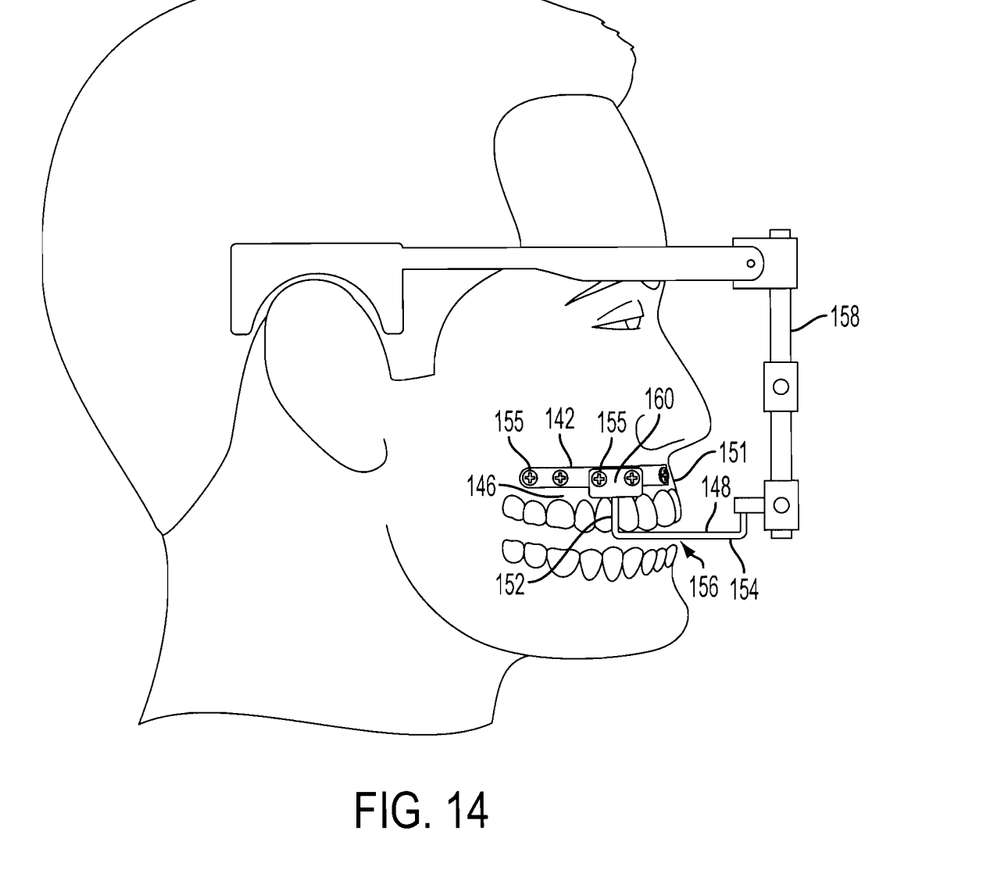
FIG. 14 is a view of the arch bar and connecting member of FIG. 13, shown coupled to a maxilla of a patient and to an external fixation member.

As described above in other embodiments, the arch bar is capable of conforming to a dental arch of a subject—in this case the upper dental arch 146 (FIG. 14). In use, arch bar 142 is bent such that it substantially conforms to the subject's upper dental arch 146. As with the other arch bars disclosed herein, arch bar 82 can be made of any suitable material capable of conforming to the dental arch, such as a metal or a plastic that is malleable or capable of conforming to a desired shape.

As shown in FIG. 13, a connecting member 148 can extend from an occlusal edge (side) 150 of arch bar 142. Connecting member 148 can be integrally formed with arch bar 142 or it can be a separate member that is coupled to arch bar 142. For example, FIG. 13 illustrates an embodiment in which connecting member 148 is secured to arch bar 142 by placing a connecting portion 160 of connecting member 148 on an outer surface 162 of arch bar 142. The connecting portion 160 comprises two fastener openings that are aligned with the fastener openings 144 of arch bar 142 and two surgical screws are passed through the aligned fastener openings, securing arch bar 142 to the maxilla and, at the same time, securing the connecting portion 160 to arch bar 142.

In a preferred embodiment, connecting member 148 is configured to have at least a portion that is substantially "L-shaped." A first portion 152 of the L-shape extends from the occlusal side 150 a sufficient length to reach a lower portion of an upper lip 151, and a second portion 154 is substantially perpendicular (e.g., ±about 30 degrees from perpendicular) to first portion 152 and extends out of the mouth 156 of the patient. Thus, as shown in FIG. 14, connecting member 148 is shaped so that when coupled to arch bar 142, connecting member 148 extends from the mouth 156 of the patient. A portion of connecting member 148 that extends outside of the mouth 156 (e.g., second portion 154) can be coupled to an external frame member 158 that is secured to the head of the patient.

FIG. 14 illustrates an embodiment in which an arch bar 142 with a connecting member 148 is secured to a patient's maxilla using fasteners 155 (e.g., surgical screws). The connecting member 148 is, in turn, coupled to an external frame member 158. External frame member 158 can comprise, for example, a conventional external fixation device, such as the External Midface Distractor that is available from the company Synthes® North America. Connecting member 148 can be coupled or otherwise secured to the external frame member 158 in any conventional manner, such as by screws, bolts, etc.

In other embodiments, connecting member 148 can be connected to an internal fixation device (not shown) in any conventional manner. Also, instead of attaching arch bar 142 to the maxilla, arch bar 142 can be coupled to the mandible in the same manner (e.g., by rotating or inverting arch bar 142) described in the various embodiments herein. In such an embodiment, connecting member 148 would extend from arch bar 142 and be coupled to an internal or external fixation device to provide a force on the mandible in substantially the same way that the arch bar system of the previous embodiment exerts a force on the maxilla.

As discussed above, the above arch bars of the present disclosure provide anchorage devices for various dental and/or surgical procedures. In addition to the procedures described above, it should be understood that the arch bars described herein can be used in other procedures where such an anchorage device can be useful or helpful.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

I claim:

1. A method for performing intermaxillary fixation in a subject, comprising:
   providing an elongated upper arch bar capable of conforming to an upper dental arch, wherein a plurality of transverse arms project from the upper arch bar and the upper arch bar further comprises a plurality of upper connectors;
   placing an inner surface of the upper arch bar against the teeth of the upper dental arch with the upper arch bar conforming to the upper dental arch of the subject and the transverse arms of the upper arch bar extending along a surface of a maxilla of the subject, and securing respective transverse arms of the upper arch bar to the maxilla with one or more fasteners secured into the bone of the maxilla;
   providing an elongated lower arch bar capable of conforming to a lower dental arch, wherein a plurality of transverse arms project from the lower arch bar and the lower arch bar further comprises a plurality of lower connectors;

placing an inner surface of the lower arch bar against the teeth of the lower dental arch with the lower arch bar conforming to the lower dental arch of the subject with the transverse arms of the lower arch bar extending along a surface of a mandible of the subject, and securing respective transverse arms of the lower arch bar to the mandible with one or more fasteners secured into the bone of the mandible; and securing one or more upper and lower connectors to one another to perform intermaxillary fixation of the subject.

2. The method of claim 1 wherein the upper connectors are upper ligature connectors and the lower connectors are lower ligature connectors, and securing one or more connectors to each other comprises securing one or more ligatures around one or more upper and lower ligature connectors to perform intermaxillary fixation.

3. The method of claim 2, wherein securing one or more ligatures around one or more upper and lower ligature connectors comprises securing a wire or elastic loop around one upper ligature connector and one lower ligature connector.

4. The method of claim 2, wherein the upper ligature connectors project from an outer surface of the upper arch bar and the lower ligature connectors project from an outer surface of the lower arch bar.

5. The method of claim 4, wherein the ligature connectors comprise hooks or studs.

6. The method of claim 1, wherein the transverse arms of the upper arch bar are movable relative to the upper arch bar, and the transverse arms of the lower arch bar are movable relative to the lower arch bar, and the method further comprises moving the transverse arms of the upper arch bars to position the arms between roots of upper teeth before securing the transverse arms of the upper arch bar to the maxilla, and moving the transverse arms of the lower arch bars to position the arms between roots of lower teeth before securing the transverse arms of the lower arch bar to the mandible.

7. The method of claim 6, wherein the transverse arms of the upper arch bar are malleable so that they are movable relative to the upper arch bar and each other, and the transverse arms of the lower arch bar are malleable so that they are movable relative to the lower arch bar and each other.

8. The method of claim 1, wherein each transverse arm of the upper arch bar comprises one or more fastener openings through which the one or more fasteners are placed to secure the arm of the upper arch bar to the maxilla, and each transverse arm of the lower arch bar comprises one or more fastener openings through which the one or more fasteners are placed to secure the arm of the lower arch bar to the mandible.

9. The method of claim 1, wherein each transverse arm of the upper arch bar comprises a first fastener opening and a second fastener opening and each transverse arm of the lower arch bar comprises a first fastener opening and a second fastener opening, the method further comprising:

aligning a transverse arm that is adjacent a fracture so that it extends across the fracture, and introducing screws in each of the first and second fastener openings of that transverse arm and into respective fracture segments to align the fracture segments.

10. The method of claim 1, further comprising adhering the upper arch bar to the upper teeth with a dental adhesive, and adhering the lower arch bar to the lower teeth with a dental adhesive.

11. A method for securing arch bars in a subject for use with orthodontic braces, comprising:

providing an elongated upper arch bar capable of conforming to an upper dental arch, the upper arch bar comprising a plurality of upper fastener openings and a plurality of upper ligature connectors, the upper fastener openings and upper ligature connectors being spaced apart from one another along a main axis of the upper arch bar;

placing an inner surface of the upper arch bar in direct contact with the mucosal surface of the upper dental arch with the upper arch bar conforming to the upper dental arch of the subject such that two or more upper fastener openings are positioned adjacent a maxilla of the subject at a location between adjacent roots of maxillary teeth;

securing the upper arch bar to the maxilla by inserting at least one fastener through at least one of the two or more upper fastener openings of the upper arch bar that are located between adjacent roots of maxillary teeth;

providing an elongated lower arch bar capable of conforming to a lower dental arch, the lower arch bar comprising a plurality of lower fastener openings and a plurality of lower ligature connectors, the lower fastener openings and lower ligature connectors being spaced apart from one another along a main axis of the lower arch bar;

placing an inner surface of the lower arch bar in direct contact with the mucosal surface of the lower dental arch with the lower arch bar conforming to the lower dental arch of the subject such that with two or more lower fastener openings of the elongated lower arch bar are positioned adjacent a mandible of the subject at a location between adjacent roots of mandibular teeth;

securing the lower arch bar to the mandible by inserting at least one fastener through at least one of the two or more lower fastener openings of the lower arch bar that are located between adjacent roots of mandibular teeth;

securing orthodontic braces to the maxillary teeth and the mandibular teeth; and securing one or more upper and lower ligature connectors to the orthodontic braces.

12. The method of claim 11, wherein the upper ligature connectors project from an outer surface of the upper arch bar and the lower ligature connectors project from an outer surface of the lower arch bar.

13. The method of claim 12, wherein the ligature connectors comprise hooks or studs.

14. The method of claim 11, wherein the upper arch bar comprises at least four upper fastener openings, and the lower arch bar comprises at least four lower fastener openings.

* * * * *